United States Patent [19]

LeVeen

[11] 4,032,860

[45] June 28, 1977

[54] RADIO FREQUENCY POWER GENERATOR HAVING ADJUSTABLE STABILIZED OUTPUT LEVEL AND FAIL-SAFE CONTROL CIRCUITS

[76] Inventor: Harry H. LeVeen, 800 Poly Place, Brooklyn, N.Y. 11209

[22] Filed: July 11, 1975

[21] Appl. No.: 595,095

[52] U.S. Cl. .................................. 331/63; 128/422; 331/183; 331/185
[51] Int. Cl.² ..................... A61N 1/40; H02H 7/20; H03B 3/02
[58] Field of Search .......... 331/182, 183, 185, 186, 331/62, 63; 128/419 R, 421, 422, 423

[56] References Cited

UNITED STATES PATENTS

| 2,448,541 | 9/1948 | Maxson | 331/63 X |
| 3,668,556 | 6/1971 | Harbeson | 331/183 X |
| 3,670,737 | 6/1972 | Pearo | 128/422 |

Primary Examiner—Siegfried H. Grimm
Attorney, Agent, or Firm—Brooks, Haidt, Haffner & Delahunty

[57] ABSTRACT

An apparatus for treating tumors, both benign and malignant, such as carcinoma, sarcoma, cysts and avascular lesions, in animals, such as humans, by radio frequency heating at the location of the tumor in the host having an adjustable, stable output level with fail-safe feature.

1 Claim, 5 Drawing Figures

U.S. Patent  June 28, 1977  4,032,860
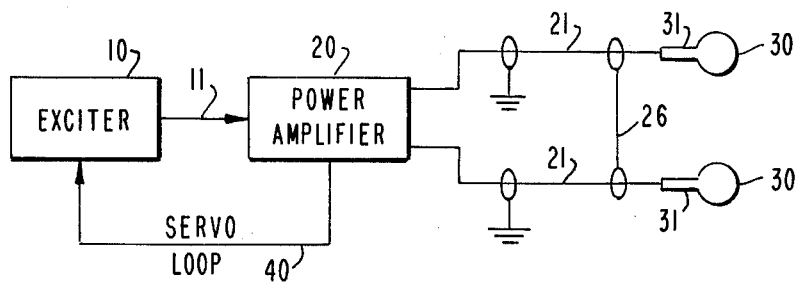
FIG.1
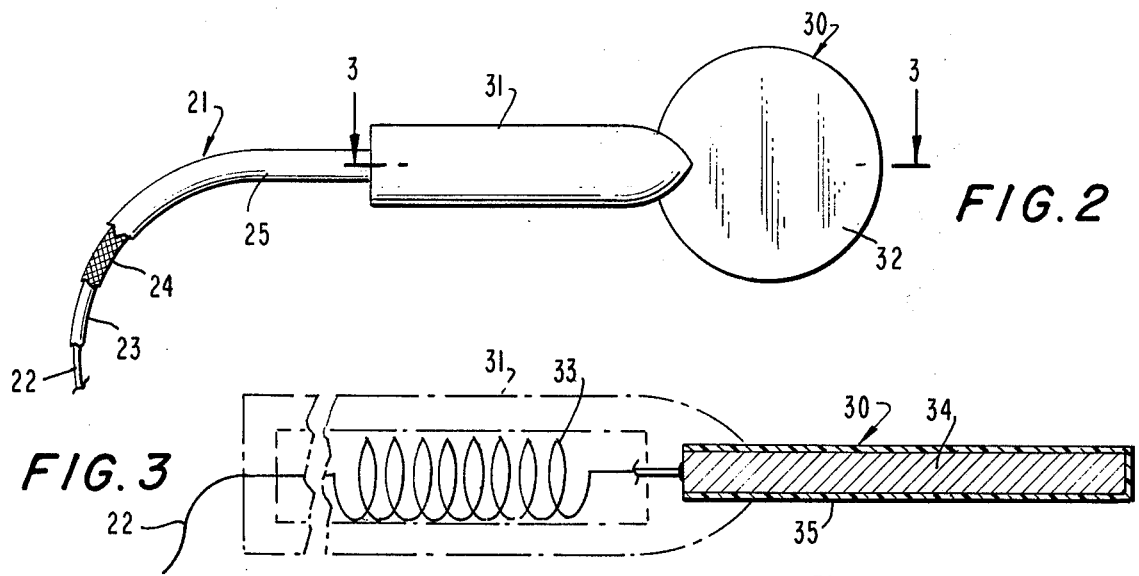
FIG.2
FIG.3
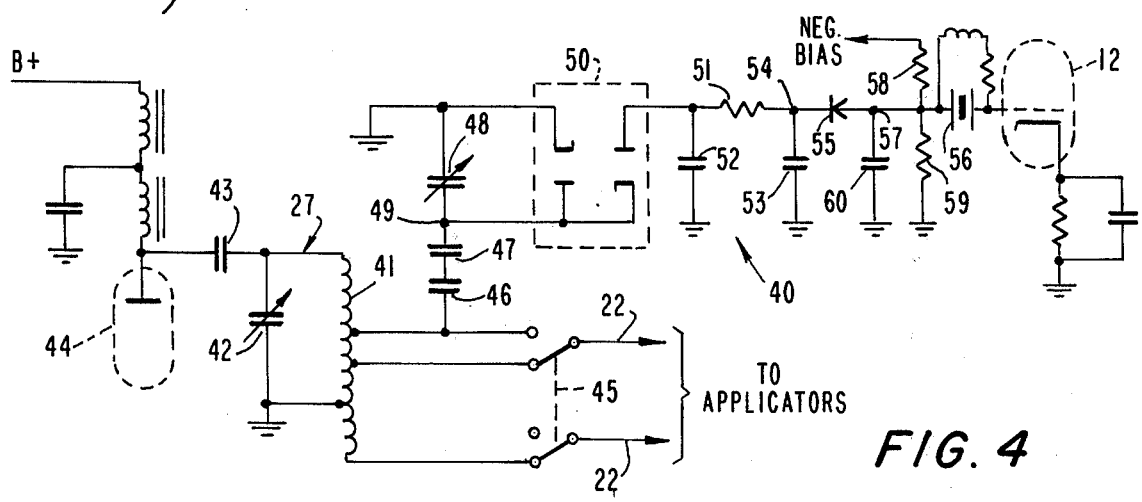
FIG.4
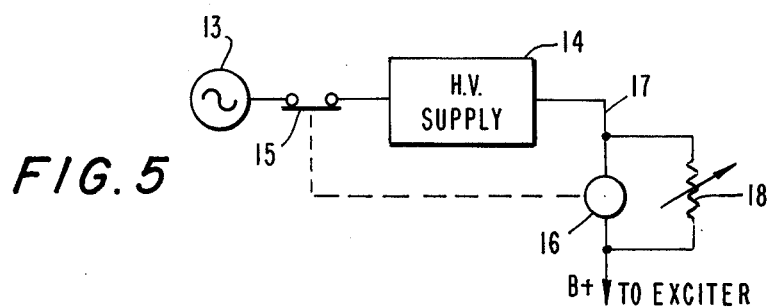
FIG.5

RADIO FREQUENCY POWER GENERATOR HAVING ADJUSTABLE STABILIZED OUTPUT LEVEL AND FAIL-SAFE CONTROL CIRCUITS

RELATED CASE

This application is related to LeVeen application Ser. No. 595,094 filed concurrently herewith, now abandoned in favor of application Ser. No. 643,661, filed Dec. 23, 1975.

This invention relates to the treatment of tumors and the like by the application of radio frequency electric power and in particular provides an apparatus for generation of radio frequency electric power having an adjustable, stable output level utilizing a servo feedback circuit and provided with a fail-safe feature in the event of loss of control in the feedback circuit.

Co-pending LeVeen application Ser. No. 595,094 filed concurrently herewith relates to the treatment of tumors in animal hosts, such as human beings, and in particular provides a technique for destroying the tumor without injury to adjacent normal tissue. The tumors can be either benign or malignant and include carcinomas, sarcomas, cysts and avascular lesions. In accordance with the above noted co-pending LeVeen application diathermy is used to produce differential heating in the body by using insulated conductive metal plates, i.e., applicators, which are connected to the output of an R.F. generator and which are placed in intimate contact with the body adjacent the location of the tumor such that the applicators are located on opposite sides of the tumor to produce localized heating in the tumor differentially higher than the remaining normal tissue, adjacent to the tumor, which is in the path of the R.F. radiation, i.e., generally between the applicators.

Generally, the radio frequencies employed should be as low as permissable in order to enhance the absorption of the energy by the tissue. Consequently, the lower frequencies permitted by the F.C.C. are preferable. Energies ranging between 200 and 500 watts and for period of times of 10 to 20 minutes typically required, although lower and higher power levels and longer and shorter periods of time can be used depending on the size and location of the tumor. The conventional diathermy machine cannot provide the necessary heat and has the disadvantage that the distribution of heat in the tissues is apt to be non-uniform and cannot always be predicted. Also a considerable amount of the energy on the standard diathermy machine is often reflected back into the diathermy machine without entering the tissue. Thus it is difficult to determine the dosage. Developing the energies required can cause overheating in a conventional diathermy machine.

It is thus an important object of this invention to provide apparatus for generating and amplifying radio frequency electric power to a sufficiently high level, i.e., up to 1000 watts, for use in the treatment of tumors in accordance with the above noted co-pending LeVeen application.

In accordance with this object it is a further object of the present invention to provide such an apparatus having a system for adjusting the level of electrical power in its output such that by simple manual control of a single element the power output level can effectively be set at any preselected value.

In accordance with this latter object, control is achieved through a negative feedback, servo loop and consequently it is also an object of this invention to provide a fail-safe feature in the event of failure of the control circuit which might otherwise result in full power application and possible injury to the patient.

In accordance with this invention, these and other objects are essentially achieved utilizing a system involving a radio frequency electrical signal source which has its output connected to the input of a radio frequency power amplifier capable a generating suitable power levels, i.e., on the order of 1000 watts, and in which the power amplifier output is a function of the amplitude of the radio frequency signal applied to its input. Control of the output level of the radio frequency power amplifier at any selected level within the capability of the amplifier is obtained despite variation in the load by sensing the output level and using a manually selected portion of the output level through a negative feedback servo loop to control the amplification in the signal source.

In such an arrangement, when operating at a reduced power level, failure of the control circuit could result in application of full power and possible injury to the patient; consequently, in accordance with this invention, provision is also made for detecting such a failure and disabling the apparatus upon detecting such failure. Such detection is accomplished by utilizing a current sensitive device such as a relay in the high voltage supply, for example, of the radio frequency electric signal source, and adjusting such relay to be responsive to an increase in current in such supply above a preselected maximum to cause the relay to operate and disconnect the high voltage supply from its external power source.

For a more complete understanding of the practical application of this invention reference is made to the appended drawings in which:

FIG. 1 is a block diagram indicating one apparatus set-up in accordance with the invention;

FIG. 2 is a plan view of an applicator suitable for use with the apparatus of FIG. 1;

FIG. 3 is an enlarged, fragmentary section taken at line 3—3 in FIG. 2;

FIG. 4 is a schematic diagram of a control circuit useful in stabilizing the power level of the apparatus shown in FIG. 1; and FIG. 5 is a block diagram of a safety circuit in order to insure fail-safe operation of the apparatus shown in FIG. 1 in the event of a breakdown in the control circuit or the like.

Referring to FIG. 1 a simple arrangement of apparatus in accordance with this invention involves an exciter 10, a power amplifier 20, and a pair of applicators 30. Both the exciter 10 and power amplifier 20 are conventional. Exciter 10 has a crystal controlled oscillator, in the illustraded case operating on 13.56 MHz. Exciter 10 has an output of between 2 watts and 110 watts dependent on the bias of the oscillator; the less negative the bias the higher the output of exciter 10.

Power amplifier 20 is designed to amplify the output of exciter 10, and to this end the output circuit of exciter 10 is connected to the input circuit of power amplifier 20 as denoted by the reference numeral 11. Power amplifier 20 is designed for an output 30 watts to 1,000 watts dependent upon the output of exciter 10 and of course, is tuned to the same frequency of 13.56 MHz.

The output circuit of power amplifier 20 is connected to energize applicators 30 by means of coaxial cables 21. Cables 21 have their inner conductors connected across the tank circuit of the output of power amplifier 20 and lead to applicators 30, as more fully described with respect to FIGS. 2 and 3. As shown in FIG. 2, each coaxial cable 21 includes a central conductor 22 which is provided with insulation 23 over which there is a braided shield 24 and an outer jacket 25. The two conductors 22 are connected across the tank coil in the output circuit of power amplifier 20, or optionally one can be grounded. In either case the two shields 24 are grounded at the power amplifier, and, as shown in FIG. 1, are preferably also provided with an interconnection 26 between shields 24 adjacent the handle 31 of each applicator 30.

Generally applicators 30, as can be seen best in FIG. 2, are in the shape of a paddle having a handle 31 and an applicator portion 32.

Each handle 31 is made of insulating material, such as a phenolic resin, and, as can be seen best in FIG. 3, is hollow such that, as coaxial cable 21 is brought into the end of handle 31, the central conductor 22 is electrically connected to a coil 33 positioned in handle 31. The applicator portion 32 is secured to handle 31 at the end of handle 31 opposite that to which conductor 22 is connected and is in the form of a flat, circular copper disc 34 which is electrically connected at its periphery adjacent the end of handle 31 to the end of coil 33 remote from connection with conductor 22.

As illustrated in FIG. 3 copper plate 34 is provided with an insulating coating 35, for example of a polyurethane resin, such that electrical contact with plate 34 can only be made through coil 33.

Two sizes of applicators 30 have presently been constructed. In one copper plate 34 is 4 inches in diameter, and in the other copper plate 34 is 2 inches in diameter. In each case copper plate 34 is about ⅛ inch thickness. In the instance of the 4 inch plate coil 33 is 6 turns with an outside diameter of ½ inch (wound about a pencil) and is ½ inch in length. Coil 33 is positioned in the center of insulated handle 31 and potted using a silicone rubber composition. In the case of the two inch copper plate 34 coil 33 is again wound about a pencil and is 18 turns having an outside diameter of ½ inch and is 1 inch in length. Again coil 33 is potted in the handle using silicone rubber composition. In each case, coil 33 is a copper wire about 20 gage AWG. In each case coaxial cable 21 is of a type known RG 58-U and is approximately 3 feet in length from power amplifier 20 to the associated applicator 30. In each case the thickness of insulated coating 35 is approximately 4 mils and is a polyurethane resin which is clear, containing no oxides.

FIG. 4 illustrates a servo control generally designated by the reference numeral 40 in FIG. 1 in which the power output of power amplifier 20 is sensed and the amplification in exciter 10 is controlled to hold the power output of amplifier 20 at any desired constant level which can be pre-selected by manual control.

In the arrangement shown in FIG. 4 the reference numeral 27 indicates the tank circuit in the output stage of power amplifier 20 which includes a tank coil 41 and tuning capacitor 42 which are adjusted to resonance at 13.56 MHz and are connected through a coupling condenser 43 to the plates of a pair of parallel output tubes indicated schematically as a single tube 44. In the illustrated case these are a pair of 3-500 Z triodes, connected as grounded-grid amplifiers, having a plate supply of approximately 2400 volts DC.

Coupling capacitor 43 is 0.001 uf and tuning capacitor 42 is a variable capacitor having 10–250 pf. Tank coil 41 has 5 turns and is grounded 1½ turns above its end remote from triodes 44 and is tapped at such end and 1½ turns above the ground tap for connection to conductors 22 through a double pole switch 45 in one mode of connection of such switch. The other mode of connection of such switch is utilized when only one applicator 30 is to be used and the other side is grounded.

Also approximately 2 turns from the high voltage end, coil 41 is tapped to withdraw the servo (sensing) signal through a voltage divider comprising a pair of serially connected capacitors 46 and 47 of 200 pf each and a third serially connected variable capacitor 48 of 50–900 pf which is in turn connected to ground.

The common connection 49 of capacitors 48 and 47 leads to a rectifier voltage doubler 50 which is a dual diode 6AL5. Connection 49 is thus to the plate of one and the cathode of the other diode, while the cathode of the first is grounded and the plate of the other leads to a filter circuit consisting of a 2.2 K ohm resistor 51 having its end adjacent the plate by-passed to ground through a 115 pf capacitor 52 and its end remote from the plate by-passed to ground through a 0.02 uf capacitor 53.

The common junction 54 of resistor 51 and capacitor 53 thus has on it a negative DC voltage which is a function of the RF voltage at junction 49 in the voltage divider comprising capacitors 46 and 47 and capacitor 48, rectified and amplified by voltage doubler 50. Junction 54 is connected through a blocking diode 55 to crystal 56 and to the grid of an oscillator tube 12 in exciter 10, which in the illustrated case is a 6Y6G.

Oscillator tube 12 is also biased at the common junction 57 of diode 55 and crystal 56 by means of a voltage divider consisting of a pair of serially connected resistors 58 and 59 which are connected, respectively, between −110 volts DC and junction 57 and between junction 57 and ground. Resistor 58 is 75 K ohm and resistor 59 is 10 K ohm. An RF by-pass capacitor 60 having 0.005 uf is also connected from common junction 57 to ground.

It will be apparent that variable capacitor 48 functions to control the amount of RF voltage impressed on voltage doubler and rectifier 50 and consequently to control the negative bias at terminal 54. Diode 55 prevents the flow of current from terminal 57 to terminal 54 when the negative bias at terminal 54 is less negative than the fixed negative bias supplied by the voltage divider formed of resistors 58 and 59 and thus limits the maximum power output of amplifier 20. When, however, the negative bias at terminal 54 goes below that at terminal 57 current flows from terminal 54 through resistor 59 to make the bias on tube 12 more negative, and hence decreases the amplification in exciter 10. This, of course, is a function of the capacitance of capacitor 48. Since the power output of amplifier 20 is a function of the bias on oscillator tube 12, servo loop 40 thus, under the control of the manual setting of capacitor 48, functions to control and hold stable the power output of amplifier 20 by controlling the voltage output of exciter 10 through control of the amplification in oscillator tube 12.

It will be apparent, however, that should there be a breakdown in the servo system oscillator 12 will be driven to full amplification as determined by the fixed bias supplied by resistors 58 and 59. As a consequence, a fail-safe circuit is supplied, as shown diagramatically in FIG. 5. In this fail-safe circuit the connection of AC supply 13 to the high-voltage DC supply 14 for exciter 10 is made through a relay operated switch 15 which is normally closed. Switch 15 is operated to open position by a relay coil 16 connected in series in the DC high voltage lead 17 to the anodes of the amplifier tubes in exciter 10. Coil 16 is shunted by an adjustable resistor 18 which functions to control the sensitivity of relay coil 16 and which is set such that, when the current flowing in line 17 exceeds a predetermined maximum, relay coil 16 will operate switches 15 to open them and break the high voltage supply.

Thus, if for any reason servo circuit 40 should fail or if for any other reason amplification in exciter 10 should suddenly increase to an undersired value, the high voltage supply 14 will be shut off and exciter 10 rendered inoperative, thereby preventing the use of power amplifier 20 until the difficulty has been located and switch 15 manually reset.

I claim:

1. In a system for applying radio frequency electrical power of selectable level to a load which includes:

a radio frequency electrical signal source having an input circuit and an output circuit for generating a radio frequency electrical signal in said output circuit, the amplitude of said signal in said output circuit being a function of the amplitude of a control signal applied to said input circuit, radio frequency power amplifier means having an input circuit and an output circuit for generating a radio frequency electric signal in said output circuit of said amplifier means having a power level which is a function of the amplitude of a radio frequency signal applied to said input circuit of said amplifier means, and said output circuit of said signal source being coupled to said input circuit of said amplifier means, the improvement in which said output circuit of said amplifier means is coupled to said input circuit of said signal source through a negative feedback servo loop including sensing means connected to said output circuit of said amplifier means for sensing the radio frequency power level in said output circuit of said amplifier means, said sensing means including manually operated control means and being connected to said input circuit of said signal source for connecting a portion of the sensed output level as a control signal for said signal source, said portion being controlled by said control means, and a high voltage supply connected to an external power source, means connecting said high voltage supply to said signal source, current sensitive means in said connecting means responsive to an increase therein above a preselected maximum to interrupt the connection between said external power source and said high voltage supply to disable said high voltage supply.

* * * * *